(12) United States Patent
Fukui et al.

(10) Patent No.: US 6,828,028 B1
(45) Date of Patent: Dec. 7, 2004

(54) MEDICAL MATERIALS AND PROCESS FOR PRODUCING THE SAME

(75) Inventors: Hiroki Fukui, Tsukuba (JP); Ken Suzuki, Tsukuba (JP); Kenshiro Shuto, Tsukuba (JP); Nobuyuki Yamamoto, Tsukuba (JP); Kazuhiko Ishihara, Kodaira (JP); Nobuo Nakabayashi, Matsudo (JP)

(73) Assignee: NOF Corporation, Tokyo (JP)

( * ) Notice: Subject to any disclaimer, the term of this patent is extended or adjusted under 35 U.S.C. 154(b) by 279 days.

(21) Appl. No.: 10/048,367

(22) PCT Filed: Jul. 24, 2000

(86) PCT No.: PCT/JP00/04921

§ 371 (c)(1),
(2), (4) Date: Jan. 25, 2002

(87) PCT Pub. No.: WO01/07097

PCT Pub. Date: Feb. 1, 2001

(30) Foreign Application Priority Data

Aug. 16, 1999 (JP) ............................................ 11-229588

(51) Int. Cl.[7] ............................................... B32B 27/38
(52) U.S. Cl. ...................... 428/413; 427/2.1; 427/2.12; 427/386; 427/402; 428/414
(58) Field of Search ................................. 428/413, 414, 428/415, 416, 417, 418; 427/2.1, 2.12, 402, 386

(56) References Cited

U.S. PATENT DOCUMENTS 5,258,481 A * 11/1993 Hesselmans et al. .......... 528/28
5,280,084 A * 1/1994 Paul .......................... 525/375

FOREIGN PATENT DOCUMENTS

| EP | 611 576 | 8/1994 | ............ A61L/29/00 |
| JP | 9-066098 | 3/1997 | ............ A61L/29/00 |
| WO | 93-01221 | 1/1993 | ......... C08F/246/00 |

* cited by examiner

Primary Examiner—Robert Dawson
Assistant Examiner—Michael Feely
(74) Attorney, Agent, or Firm—Darby & Darby

(57) ABSTRACT

A medical material having a surface which is safe and excellent in stability with the lapse of time and has a high durability as needed in establishing a long-lasting surface lubricity in a wet state and an excellent compatibility with blood, and a method for producing the same. These materials are obtained by forming a coating layer with a coating material containing a polymeric substance (A) having a heterocyclic group represented by the formula (1) on at least a part of a surface of a medical material base, and then ring-opening the heterocyclic group remaining in the coating layer by a nucleophilic compound (N):

$$\begin{array}{c} R^1 \quad H \\ | \quad \;\; | \\ -C-C-H \\ \diagdown\!\diagup \\ X \end{array} \tag{1}$$

wherein X represents O, NH or S; and $R^1$ represents H or $CH_3$.

11 Claims, No Drawings

MEDICAL MATERIALS AND PROCESS FOR PRODUCING THE SAME

This application is a national phase application under 35 U.S.C. §371 of International Application No. PCT/JP00/04921, filed Jul. 24, 2000, which was published on Feb. 1, 2001 as International Publication No. WO 01/07097, and claims the benefit of Japanese Patent Application No. 11/214191, filed Jul. 28, 1999, and Japanese Patent Application No. 11/229588, filed Aug. 16, 1999.

FIELD OF ART

The present invention relates to a medical material having both the surface lubricity and blood compatibility with a coating layer that is safe and excellent in stability with the lapse of time, and a process for producing the same.

BACKGROUND ART

There have hitherto been made various researches on surface treatment methods for modifying and improving the surface function of a material constituting a medical instrument. Particularly, it is important that a medical instrument for use in direct contact with blood has a surface with an improved blood compatibility in order to minimize the performance degradation of the medical instrument due to the formation of thrombus, and the occurrence of serious complication due to the separation of thrombus from the surface of the base material. In addition to the blood compatibility, medical instruments, e.g. a catheter to be directly inserted from outside of the body into a blood vessel, and a guidewire for guiding the catheter to a target site in the blood vessel, are required to have a surface lubrication from the viewpoint of the improvement of the operability, and the reduction of damage of a tissue such as a blood vessel.

As the most practical method for imparting these functions to the surface of a medical instrument, there have been made various researches on surface modification methods by means of a hydrophilic polymer. The surface modification of the medical instrument with a hydrophilic polymer may preferably be chemical fixation of the hydrophilic polymer on the surface of the base material rather than simple coating for the safety and the persistence of the effect. A large number of researches have hitherto been made on the method for fixing the hydrophilic polymer onto the surface of the base material. Among them, there has been proposed a method utilizing a surface coupling reaction using an epoxy group.

As an example of the improvement of the blood compatibility of a medical instrument by fixing a hydrophilic polymer through an epoxy group, Japanese Laid-Open Patent Publication No. JP-A-7-184989 discloses a method in which either of (i) the polymeric material obtained by crosslinking a copolymer of 2-(methacryloyloxy)ethyl-2'-(trimethylammonio)ethyl phosphate (below, abbreviated as MPC) and an epoxy-group containing monomer with a compound having two or more groups of at least either of an amino group and a carboxyl group; or (ii) the polymeric material obtained by crosslinking a copolymer of MPC and at least one monomer of an amino group-containing monomer and a carboxyl group-containing monomer with a compound having two or more epoxy groups is attached to the surface of a medical material. Japanese Laid-Open Patent Publication No. JP-A-7-184990 discloses a method in which a copolymer of MPC, an epoxy group-containing monomer, and at least one monomer of a hydroxyl group-containing monomer, an amino group-containing monomer, and a carboxyl group-containing monomer is fixed on the surface of a base material.

However, the resulting crosslinked film of MPC copolymer after the heat treatment in any of the foregoing methods has high possibility to contain highly toxic residual epoxy groups, which may give a harmful effect on the human body when the film is located in the body.

Japanese National Phase PCT Laid-Open Publication No. JP-A-7-502053 (WO93/01221) discloses an MPC polymer having a pendant group for stably binding the polymer to a surface, a production method thereof, and a method for giving biocompatibility on the surface by binding the polymer to a base material.

However, this method also has a problem in terms of safety when the pendant group is an epoxy group. Further, any studies on the surface lubricity have not been done for any of the aforementioned materials to which the MPC polymers have been bound, and there is thus no description on the function.

For the surface lubrication of a medical instrument using a hydrophilic polymer, for example, the following methods are disclosed: a method in which a surface of a base material having a proton donating group capable of reacting with the reactive functional group is coated with a water-swellable polymer having a reactive functional group in the molecule (Japanese Laid-Open Patent Publication No. JP-A-6-285152); a method in which, onto a medical instrument surface made of a base material of a synthesized polymer having an acid anhydride in its molecule, a water-swellable polymer having a functional group capable of reacting with the acid anhydride is fixed (Japanese Laid-Open Patent Publication No. JP-A-7-204262); a method in which an insolubilized product of a mixture of a hydrophilic polymer having a reactive functional group in its molecule and a polymer having a functional group capable of reacting with the reactive functional group is formed on the surface of a base material of a medical instrument (Japanese Laid-Open Patent Publication No. JP-A-8-24327); a method in which, onto the base surface of a medical instrument made of polyolefin or modified polyolefin, a mixture of a resin having adhesiveness to the polyolefin or the modified polyolefin and an insolubilized product of a hydrophilic polymer having a reactive functional group in its molecule is bound, or a method in which the hydrophilic polymer is bound to the base surface through the adhesive resin (Japanese Patent Laid-Open Publication No. JP-A-8-24328); a method in which a water soluble or water swellable polymer is immobilized by forming an interpenetrating network structure (IPN) with the base of a medical instrument (Japanese Patent Laid-Open Publication No. JP-A-8-33704); a method in which a hydrogel made of an insolubilized product of a water soluble or water swellable polymer having a reactive functional group in the molecule and an antithrombotic agent is formed on the surface of a medical instrument (Japanese Patent Laid-Open Publication No. JP-A-8-19599); a method in which a hydrophilic polymer having a reactive heterocyclic group is immobilized on the base surface of a medical instrument to which a functional group reactive with the reactive heterocyclic group has previously been introduced (WO90/01344); and a method in which a copolymer containing ω-carboxy(meth)acrylate and an epoxy group-containing vinyl monomer is immobilized on the base surface of a medical instrument onto which a polymer having a proton donating group reactive with an epoxy group has previously been applied (Japanese Patent Laid-Open Publication No. JP-A-10-20180).

With any of these methods, when the polymer involved in the lubricity is a hydrophilic polymer having an epoxy group in its molecule, the crosslinking in the coating film may occur with the lapse of time, which results in lowering of the water holding capacity of the film, and loss of the wet surface lubricity of the film. In addition to such a problem of the time-dependent degradation of the product performance, there is also a problem in terms of safety. Further, all the various lubricated surfaces described above have insufficient blood compatibility.

DISCLOSURE OF THE INVENTION

It is an object of the present invention to provide a medical material having the surface which is safe and excellent in stability with the lapse of time, which has both a high durability that is necessary for establishing a long-lasting surface lubricity in a wet state as well as an excellent compatibility with blood, and a production method thereof.

According to the present invention, there is provided a medical material obtained by forming a coating layer with a coating material containing a polymeric substance (A) having a heterocyclic group represented by the formula (1) on at least a part of a surface of a medical material base, and ring-opening the heterocyclic group remaining in the coating layer by a nucleophilic compound (N):

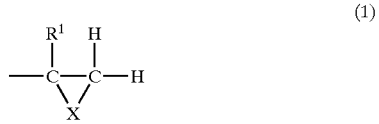

(1)

(wherein X denotes O, NH, or S, and $R^1$ denotes H or $CH_3$).

According to the present invention, there is also provided a medical material obtained by forming a coating layer with a coating material containing a polymeric substance (A) having a heterocyclic group represented by the aforementioned formula (1) on at least a part of a surface of a medical material base, providing on the coating layer a coating film configured with a hydrophilic copolymer (B) having a reactive functional group capable of reacting with the heterocyclic group, and ring-opening the heterocyclic group remaining in the coating layer by a nucleophilic compound (N).

According to the present invention, there is further provided a method for producing the medical material, which includes the step of applying a coating material containing a polymeric substance (A) having a heterocyclic group represented by the aforementioned formula (1) on at least a part of a surface of a medical material base, followed by heating to form a coating layer, and the step of bringing the coating layer into contact with a solution containing a nucleophilic compound (N) to ring-open the heterocyclic group remaining in the coating layer.

According to the present invention, there is still further provided a method for producing the medical material, which includes the step of applying a coating material containing a polymeric substance (A) having a heterocyclic group represented by the aforementioned formula (1) on at least a part of a surface of a medical material matrix, followed by heating to form a coating layer, the step of applying on the coating layer a solution of a hydrophilic copolymer (B) having a reactive functional group capable of reacting with the heterocyclic group, followed by heating to provide a coating film configured with the hydrophilic copolymer (B), and the step of bringing the coating layer into contact with a solution containing a nucleophilic compound (N) to ring-open the heterocyclic group remaining in the coating layer.

PREFERRED EMBODIMENTS OF THE INVENTION

The medical material of the present invention is the one obtained by forming a coating layer with a coating material containing a polymeric substance (A) having a heterocyclic group represented by the aforementioned formula (1) on at least a part of the surface of a medical material base, and ring-opening the heterocyclic group remaining in the coating layer by a nucleophilic compound (N); or the one obtained by forming a coating layer with a coating material containing the polymeric substance (A) on at least a part of the surface of a medical material base, providing on the coating layer a coating film configured with a hydrophilic copolymer (B) having a reactive functional group capable of reacting with the heterocyclic group, and ring-opening the heterocyclic group remaining in the coating layer by a nucleophilic compound (N).

The heterocyclic groups represented by the formula (1) present in one molecule of the polymeric substance (A) may be the same or different groups. The heterocyclic groups may include ethylene oxide group, propylene oxide group, ethyleneimine group, propyleneimine group, ethylene sulfide group, and propylene sulfide group.

There is no limitation as to the polymeric substance (A) so long as it has the heterocyclic group. For example, a polymeric substance having a physical property of hydrophilicity or water swellability is desirably used for imparting the functions such as the antithrombogenic property and the surface lubricity to the resulting coating layer on the surface of the base of a medical material. Examples of methods for producing the hydrophilic polymeric substance having the heterocyclic group may include (A-1) a method in which a compound having the heterocyclic group is allowed to react with a hydrophilic polymeric substance to introduce the heterocyclic group thereon; and (A-2) a method in which a hydrophilic radical polymerizable monomer (a1) and a heterocyclic group-containing monomer (a2) are copolymerized.

The hydrophilic polymeric substance to be used in the method (A-1) may be either a natural polymer or a synthetic polymer. Examples of the natural polymers may include polysaccharides and proteins.

Examples of the polysaccharides may include carboxymethyl starch, dialdehyde starch, pullulan, mannan, amylopectin, amylose, dextran, hydroxyethyl dextran, levan, inulin, chitin, chitosan, xyloglucan, alginic acid, gum arabic, guar gum, gum tragacanth, hyaluronic acid, heparin, methyl cellulose, ethyl cellulose, cellulose acetate, nitrocellulose, carboxymethyl cellulose, carboxymethyl ethyl cellulose, hydroxyethyl cellulose, hydroxypropyl cellulose, ethyl hydroxyethyl cellulose, and hydroxypropyl methyl cellulose.

Examples of the proteins may include glue, gelatin, casein and collagen.

Examples of the synthetic polymers may include polyvinyl alcohol, sodium polyacrylate, polyethylene oxide, polyacrylamide, polyethylene imine, sodium polystyrene sulfonate, a methyl vinyl ether-maleic anhydride copolymer, and a half alkyl ester of a methyl vinyl ether-maleic anhydride copolymer.

Examples of the compounds having the heterocyclic group may include an alkyl halide having the heterocyclic group represented by the following formula (3):

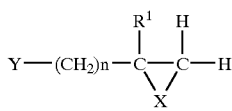

In the formula (3), X denotes O, NH, or S, Y denotes Cl, Br, or I, $R^1$ denotes H or $CH_3$, and n denotes an integer of 1 to 20.

The method (A-1) may be performed by, for example, a known method in which a hydrophilic polymeric substance and a compound having a heterocyclic group are dehydrohalogenated in the presence of a basic catalyst such as triethylamine or pyridine in an suitable aprotic organic medium for dissolving or swelling the hydrophilic polymeric substance, to obtain an objective hydrophilic polymeric substance having a heterocyclic group (referred to hereinbelow as an HC polymer).

In the method (A-1), although the amount of the compound having a heterocyclic group to be introduced may suitably selected according to an objective performance, it is preferably from 0.01 to 70 wt %, and in particular preferably from 0.1 to 50 wt % based on the amount of the hydrophilic polymeric substance. Introduction of the compound having a heterocyclic group in the amount less than 0.01 wt % may cause reduction of the reaction efficiency of the reactive functional group with the heterocyclic group present on the base material surface of the medical material, and the reduction of the crosslinking efficiency between the HC polymers, which may result in undesirable difficulty in the formation of the stable coating film. On the other hand introduction of the compound having a heterocyclic group in the amount exceeding 70 wt % may lower the function of the hydrophilic polymeric substance, thus not being preferable. In producing the medical material of the present invention, only one sort of polymer or mixture of two or more of the polymers may be used as the HC polymers.

Examples of the hydrophilic radical polymerizable monomer (a1) to be used in the method (A-2) may include a radical polymerizable monomer having a group represented by the following formula (2):

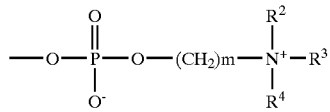

In the formula (2), $R^2$, $R^3$, and $R^4$ may be the same or different groups, and denote H, or a monovalent hydrocarbon group having 1 to 4 carbon atoms; and m is an integer of 2 to 4.

Examples of the radical polymerizable monomers (a1) having the group represented by the formula (2) may include 2-(meth)acryloyloxyethyl-2'-(trimethylammonio)ethyl phosphate (including MPC), 3-(meth)acryloyloxypropyl-2'-(trimethylammonio)ethyl phosphate, 4-(meth)acryloyloxybutyl-2'-(trimethylammonio)ethyl phosphate 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(trimethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylammonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate, 6-(meth)acryloyloxyhexyl-4'-(trimethylammonio)butyl phosphate, 2-(vinyloxy)ethyl-2'-(trimethylammonio)ethyl phosphate, 2-(allyloxy)ethyl-2'-(trimethylammonio)ethyl phosphate, 2-(p-vinylbenzyloxy)ethyl-2'-(trimethylammonio)ethyl phosphate, 2-(p-vinylbenzoyloxy)ethyl-2'-(trimethylammonio)ethyl phosphate, 2-(styryloxy)ethyl-2'-(trimethylammonio)ethyl phosphate, 2-(p-vinylbenzyl)ethyl-2'-(trimethylammonio)ethyl phosphate, 2-(vinyloxycarbonyl)ethyl-2'-(trimethylammonio)ethyl phosphate, 2-(allyloxycarbonyl)ethyl-2'-(trimethylammonio)ethyl phosphate, 2-(acryloylamino)ethyl-2'-(trimethylammonio)ethyl phosphate, 2-(vinylcarbonylamino)ethyl-2'-(trimethylammonio)ethyl phosphate, 2-(allyloxycarbonylamino)ethyl-2'-(trimethylammonio)ethyl phosphate, 2-(butyroyloxy)ethyl-2'-(trimethylammonio)ethyl phosphate, 2-(crotonoyloxy)ethyl-2'-(trimethylammonio)ethyl phosphate, ethyl-(2'-trimethylammonioethylphosphorylethyl)fumarate, butyl-(2'-trimethylammonioethylphosphorylethyl)fumarate, and hydroxyethyl-(2'-trimethylammonioethylphosphorylethyl) fumarate.

The MPC is represented by the following formula (4):

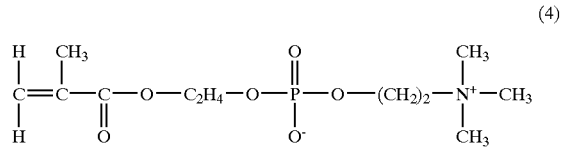

The hydrophilic radical polymerizable monomer (a1) may also be the one which does not have the group represented by the formula (2). Examples of such radical polymerizable monomers (a1) may include hydroxyalkyl(meth)acrylate monomers such as 2-hydroxyethyl(meth)acrylate and 2-hydroxypropyl(meth)acrylate; polyalkylene glycol(meth) acrylate monomers such as diethylene glycol mono(meth)acrylate, polyethylene glycol mono(meth)acrylate, polypropylene glycol mono(meth)acrylate, methoxydiethylene glycol(meth)acrylate, methoxypolyethylene glycol(meth) acrylate, and methoxypolypropylene glycol(meth)acrylate; ω-carboxy(meth)acrylates such as phthalic acid monohydroxyethyl(meth)acrylate, hexahydrophthalic acid monohydroxyethyl(meth)acrylate, ω-carboxy-polycaprolactone (n=2 to 5) mono(meth)acrylate, and (meth)acryloyloxyethyl succinate; N-vinyl-2-pyrrolidone, vinylpyridine, (meth)acrylamide, (meth)acrylic acid, 2-acrylamide-2-methylpropanesulfonic acid, dimethylaminoethyl(meth)acrylate, diethylaminoethyl (meth)acrylate, maleic anhydride, and glyco-2-hydroxyethyl monomethacrylate (GEMA). These monomers may be used singly or as a mixture thereof.

The heterocyclic group-containing monomer (a2) to be used in the method (A-2) is a monomer having a polymerizable double bond and a heterocyclic group in its molecule. Examples thereof may include glycidyl acrylate (abbreviated hereinbelow as GA), glycidyl methacrylate (abbreviated hereinbelow as GMA), methyl glycidyl methacrylate, and allyl glycidyl ether. These heterocyclic group-containing monomers (a2) may be used singly or as a mixture thereof.

In the copolymer obtainable by the method (A-2) (abbreviated hereinbelow as an HC copolymer), another radical polymerizable monomer (a3) may be copolymerized as a third component in order to control the physical properties of a coating film formed by applying the copolymer on the surface of a medical material.

The other monomer (a3) has no particular restriction. Examples thereof may include (meth)acrylic acid ester monomers such as methyl(meth)acrylate, ethyl(meth)acrylate, propyl(meth)acrylate, butyl(meth)acrylate, hexyl(meth)acrylate, lauryl(meth)acrylate, and stearyl(meth)acrylate; styrene monomers such as styrene, methyl styrene, and substituted styrene; vinyl ether monomers such as ethyl vinyl ether and N-propyl vinyl ether; vinyl ester monomers such as vinyl acetate; unsaturated hydrocarbon monomers or substituted unsaturated hydrocarbon monomers such as vinyl chloride, vinylidene chloride, ethylene, propylene, and isobutylene; and acrylonitrile. The other monomers may be used singly or as a mixture thereof.

Although the ratio of the unit derived from the monomer (a1) in the HC copolymer has no particular restriction, it is preferably from 5 to 99.9 mol %, and in particular preferably from 20 to 95 mol % based on the whole HC copolymer. If the ratio of the unit derived from the monomer (a1) is less than 5 mol %, undesirably, the performance of the monomer (a1) may not be sufficiently incorporated in the HC copolymer. On the other hand, if it exceeds 99.9 mol %, the ratio of the unit derived from the monomer (a2) in the HC copolymer inevitably becomes less than 0.1 mol %, so that the problem described below may undesirably occur.

Although the ratio of the unit derived from the monomer (a2) in the HC copolymer has no particular restriction, it is preferably from 0.1 to 95 mol %, and in particular preferably from 5 to 70 mol % based on the whole HC copolymer. If the ratio of the unit derived from the monomer (a2) is less than 0.1 mol %, the introduction efficiency into the base surface of a medical material, and the efficiency of the crosslinking reaction between the HC copolymers may be reduced, which may result in undesirable difficulty in the formation of the stable coating film. On the other hand, if it exceeds 95 mol %, the ratio of the unit derived from the monomer (a1) in the HC copolymer is relatively reduced, so that the foregoing problem may undesirably occur.

The ratio of the unit derived from the other monomer (a3) is desirably less than 70 mol % based on the whole HC copolymer in order not to damage the performance of the HC copolymer.

The characteristics of the HC copolymer may be made desirable by suitably selecting the hydrophilic radical polymerizable monomer (a1) to be used. Particularly, the HC copolymer containing a radical polymerizable monomer having the group represented by the formula (2) as a side chain, preferably the HC copolymer containing MPC as its structural unit, has excellent blood compatibility. Therefore, by providing a coating film made of the copolymer on the base material surface, it is possible to obtain a medical material satisfying both the surface lubricity and the antithrombogenic property.

The HC copolymer may be obtained, for example, by radical polymerization of a monomer composition containing the monomer (a1), the monomer (a2), and the optional other monomer (a3) in a solvent in the presence of a polymerization initiator. The radical polymerization may be performed in a system replacing the atmosphere with an inert gas such as nitrogen, carbon dioxide, or helium.

There is no limitation as to the polymerization initiator. A conventional polymerization initiator for radical polymerization may be used. Examples of the initiators may include organic peroxides such as t-butyl peroxypivalate, t-butyl peroxyneodecanoate, t-butyl peroxy-2-ethyl hexanoate, t-butyl peroxyacetate, 1,1,3,3-tetramethylbutyl peroxy-2-ethylhexanoate, succinic acid peroxide, benzoyl peroxide, 3,5,5-trimethyl hexanoyl peroxide, and lauroyl peroxide; azo compounds such as 2,2'-azobisisobutyronitrile, 2,2'-azobis(2-amidinopropane)dihydrochloride, dimethyl 2,2'-azobisisobutyrate, 2,2'-azobis(2,4-dimethylvaleronitrile), 1,1'-azobis(cyclohexane-1-carbonitrile), and 2,2'-azobis(2-methyl-N-(2-hydroxyethyl)-propionamide; persulfates such as potassium persulfate, sodium persulfate, and ammonium persulfate; and persulfate-hydrogen sulfite system. These polymerization initiators may be used singly or as a mixture thereof.

The amount of the polymerization initiator to be used is desirably from 0.001 parts by weight to 10 parts by weight, and more preferably from 0.01 parts by weight to 5 parts by weight per 100 parts by weight of the total amount of the monomers.

There is no particular limitation as to the solvent for producing the HC copolymer so long as it is a solvent which dissolves the monomers serving as structural units of the copolymer, and does not react with a heterocyclic group. The solvent may be a mixed solvent.

The HC copolymer may be purified by a general purification method such as reprecipitation, dialysis, or ultrafiltration.

In the polymeric substance (A) to be used in the present invention, the preferred weight average molecular weight of the HC copolymer is from 5000 to 5000000, and particularly from 10000 to 2000000. If the molecular weight is less than 5000, the number of the heterocyclic groups contained per molecule is inevitably reduced. As a result, the introduction efficiency of the copolymer into the base surface may be reduced. In addition, the crosslinking efficiency between the copolymers may also be reduced. Accordingly, the reduction of the coating film strength resulting therefrom may undesirably occur. If the molecular weight exceeds 5000000, the solution viscosity of the composition made of the copolymer may be increased, so that it may become difficult to handle, as well as it is likely to cause coating unevenness when applied onto the base material. The structure of the HC copolymer as the polymeric substance (A) to be used in the present invention may be any of random, block, and graft. In the polymeric substance (A), the HC copolymers may be used singly, or as a mixture of two or more copolymers.

The hydrophilic copolymer (B) to be used in the present invention is a polymeric compound which has a functional group capable of reacting with the heterocyclic group in the polymeric substance (A), and absorbs water by being in contact with a aqueous medium such as a body fluid and blood to express lubricity.

The hydrophilic copolymer (B) may be produced by, e.g., copolymerizing a hydrophilic radical polymerizable monomer (b1) and a radical polymerizable monomer (b2) having a functional group reactive with a heterocyclic group and capable of opening the ring of the heterocyclic group.

Preferable examples of the monomers (b1) may include the hydrophilic radical polymerizable monomers (a1) described above, and the mixtures thereof.

The monomer (b2) may be a radical polymerizable monomer having a functional group capable of reacting with a heterocyclic group such as a hydroxyl group, a carboxyl group, an amino group, and a thiol group, in the molecule. Examples of such compounds may include hydroxyl group-containing monomers such as 2-hydroxyethyl(meth)acrylate, 2-hydroxypropyl(meth)acrylate, polyethylene glycol mono(meth)acrylate, polypropylene glycol mono(meth)acrylate, glycerol α-mono(meth)acrylate, allyl alcohol, 2-allyl phenol, glycerol-α-monoallyl ether, ethylene glycol monoallyl ether, and N-(hydroxymethyl)acrylamide; carboxyl group-containing monomers such as (meth)acrylic acid, 3-pentenoic acid, 4-pentenoic acid, 3-allyloxypropionic acid and 2-(meth)acyloyloxyethyl phthalate; and amino group-containing monomers such as allylamine, allylamine(hydrochloride), allyl urea, 1-allyl-2-thiourethane, 2-methyl allylamine(hydrochloride), 2-aminoethyl(meth)acrylate(hydrochloride), 4-aminostyrene, and acrylamide. Use of the allylamine (hydrochloride) is particularly preferred in terms of high reactivity with the heterocyclic group, and availability. These monomers may be used singly or as a mixture thereof when used.

In the production of the hydrophilic copolymer (B), a radical polymerizable monomer (b3) other than the aforementioned radical polymerizable monomers may be copolymerized with the monomers (b1) and (b2). Examples of the monomers (b3) may include the aforementioned other radical polymerizable monomers (a3), and mixtures thereof.

The ratio of the unit derived from the monomer (b1) in the hydrophilic copolymer (B) is preferably from 20 to 99.9 mol %, and in particular preferably from 50 to 99 mol % based on the whole hydrophilic copolymer (B). If the ratio of the unit derived from the monomer (b1) is less than 20 mol %, the water absorbing ability of the hydrophilic copolymer (B) may be reduced, which may result in insufficient lubricity of the wet copolymer, and insufficient blood compatibility. Whereas, if it exceeds 99.9 mol %, the ratio of the unit derived from the monomer (b2) involved in the bond with the heterocyclic group is relatively reduced, so that the problem described below may undesirably occur.

The preferred ratio of the unit derived from the monomer (b2) in the hydrophilic copolymer (B) is from 0.1 to 80 mol %, and particularly from 1 to 50 mol %. If the ratio of the unit derived from the monomer (b2) is less than 0.1 mol %, the reaction efficiency with the heterocyclic group in the polymeric substance (A) may be reduced, which may result in lack of the amount of the hydrophilic copolymer (B) for exhibiting function. Even if the hydrophilic copolymer (B) is immobilized, the number of bonding points with the polymeric substance (A) may be small, so that a problem may undesirably occur in terms of durability. On the other hand, if it exceeds 80 mol %, undesirably, the characteristics of the monomer (b1) may not be sufficiently incorporated in the hydrophilic copolymer (B) as described above.

The ratio of the unit derived from the other monomer (b3) is desirably less than 50 mol % based on the total amount of the structural units of the hydrophilic copolymer (B) in order to keep desirable performance of the hydrophilic copolymer (B).

The characteristics of the hydrophilic copolymer (B) to be used in the present invention may be made desirable by suitably selecting the monomer (b1) to be used. Particularly, the hydrophilic copolymer (B) containing a radical polymerizable monomer having a group represented by the formula (2), preferably the hydrophilic copolymer (B) containing a structural unit based on MPC, has excellent blood compatibility. Therefore, by providing a coating film made of the copolymer on the base surface, it is possible to obtain a medical material satisfying both the surface lubricity and the antithrombogenic property.

The hydrophilic copolymer (B) may be produced in the same manner as the aforementioned production method of the HC copolymer. As the solvents to be used therefor, all the solvents may be used so long as they are solvents which dissolve the monomers serving as structural units of the hydrophilic copolymer (B), and a mixed solvent is also acceptable.

The weight average molecular weight of the hydrophilic copolymer (B) is preferably from 5000 to 5000000, and in particular preferably from 10000 to 2000000. If the molecular weight is less than 5000, the number of the functional groups capable of reacting with the heterocyclic groups contained per molecule is inevitably reduced. As a result, the introduction efficiency on the polymeric substance (A) previously immobilized on the matrix surface may be undesirably reduced. Whereas, if the molecular weight exceeds 5000000, problems may undesirably be occur in terms of handling of the polymer solution and coating unevenness as described above. The hydrophilic copolymer (B) may be in any of random, block, and graft forms. The hydrophilic copolymers (B) may be used singly, or as a mixture of two or more thereof.

As the medical material base (abbreviated hereinbelow as a base (M)) to be used in the present invention, any usual materials for medical instruments may be employed. It is desirable that the base (M) has a functional group such as an amino group, a hydroxyl group, or a carboxyl group reactive with a heterocyclic group on its surface. The material which has no functional group capable of being bonded to a heterocyclic group may preferably be used after forming the functional group on the surface of the base (M) by a known surface modifying method.

The method of surface modification may suitably be selected depending on the base (M) to be used. The method may include plasma processing methods such as corona discharge and glow discharge; a chemical treatment with a concentrated sulfuric acid solution containing a dichromic acid (applicable to a nonpolar polymer), partial hydrolysis of an amide linkage or an urethane linkage by an acid or an alkaline solution (applicable to polyamide and polyurethane), and application or blending of a compound having a functional group.

For the foregoing reason, the base (M) usable in the present invention has a very limited restriction. Examples of the base (M) may include without limitation polyethylene, polypropylene, polystyrene, polyvinyl chloride, nylon, polyurethane, polyurea, poly(meth)acrylic acid, poly(meth)acrylic acid ester, polyester, polyacrylonitrile, polyacrylamide, polyvinyl acetate, polycarbonate, polysulfone, polyvinyl alcohol, cellulose, cellulose acetate, silicone resin, glass, ceramics, metals, and stainless steel. Further, these base materials may be used singly, or these may be used in combination thereof as the base (M).

Then, the medical material of the present invention will be described by reference to its production method.

In the production of the medical material of the present invention, at least a part of the surface of the base (M) is coated with a coating material containing the polymeric substance (A), or the combination of the polymeric substance (A) and the hydrophilic copolymer (B), to form a coating layer.

The coating layer may be formed by, for example, dissolving the coating material in a suitable solvent, applying the resulting solution onto the surface of the base (M), and then drying and heating it thereby binding the coating layer onto the surface of the base (M).

As the solvents, any solvents which dissolve the polymeric substance (A) may be used, and a mixed solvent is also acceptable.

In the solution in which the coating material is dissolved in the solvent, the preferred concentration of the polymeric substance (A) is from 0.01 to 30 wt %, and particularly from 0.1 to 20 wt %. If the concentration is less than 0.01 wt %, the amount of the polymeric substance (A) remaining on the surface of the base (M) after the application may be insufficient, which may undesirably result in insufficient performance. On the other hand, if it exceeds 30 wt %, the solution viscosity may be increased, which may undesirably result in the poor workability upon coating, and the unevenness of the coating film.

When the hydrophilic copolymer (B) is used, a mixed solution may be prepared by dissolving each of the polymeric substance (A) and the hydrophilic copolymer (B) in separate solvents, and mixing the solutions immediately before use. As the solvents, any solvents which can dissolve both the polymeric substance (A) and the hydrophilic copolymer (B) may be employed, and a mixed solvent is also acceptable.

The preferred concentration of the polymeric substance (A) or the hydrophilic copolymer (B) in the solution before mixing is from 0.01 to 15 wt %, and particularly from 0.1 to 10 wt %. If the concentration is less than 0.01 wt %, application of the mixed solution of the polymeric substance (A) and the hydrophilic copolymer (B) may result in insufficient presence of each component on the surface of the base, and may thus result in undesirably insufficient expression of the objective performance. If the concentration exceeds 15 wt %, the solution viscosity may be increased upon preparation of the mixed solution, which may result in undesirably poor workability of coating, and unevenness of the coating film.

The mixing ratio of the solution of the polymeric substance (A) to the solution of the hydrophilic copolymer (B) may suitably be selected depending on the concentrations of solutions to be used, molecular weights, the content of the heterocyclic group in the polymeric substance (A), and the content of the functional group reactive with the heterocyclic group of the hydrophilic copolymer (B). Preferable range of the ratio of the polymeric substance (A) in the solution:the hydrophilic copolymer (B) in the solution may be 1:0.01 to 1:100.

Examples of the methods for applying the solution of the coating material may include publicly known methods such as dipping method, spray method, roller coating method, and spin coating method.

Drying may be carried out in accordance with a conventional method such as forced-air drying or drying under reduced pressure for the purpose of transpiration of the solvent.

The preferred heating condition is such a condition that the heterocyclic group in the polymeric substance (A) reacts with the functional group present on the surface of the base (M) to chemically immobilize the polymeric substance (A) on the surface of the base (M), and simultaneously the proton donating group formed by the ring-opening of the heterocyclic group reacts with the heterocyclic group to form a certain degree of a three-dimensional network structure; or such a condition that the heterocyclic group in the polymeric substance (A) reacts with the functional group present on the surface of the base (M) to chemically immobilize the polymeric substance (A) on the surface of the base (M), and simultaneously the crosslinking reaction between the polymeric substances (A) and the crosslinking reaction between the polymeric substance (A) and the hydrophilic copolymer (B) are promoted, so that a coating layer having an excellent durability is structured. The heating temperature is preferably from room temperature to 200° C., and the treatment time is preferably from 1 minute to 48 hours.

Other than the foregoing method, the coating with the coating material for producing the present medical material may also be carried out by forming a coating layer with a coating material containing the polymeric substance (A) on at least a part of the surface of the base (M), and then providing a coating film comprised of the hydrophilic copolymer (B) on the coating layer.

The coating layer with a coating material containing the polymeric substance (A) may be formed in the same manner as the aforementioned method. The coating film comprised of the hydrophilic copolymer (B) may also be provided on the coating layer in accordance with the method for forming the coating layer.

By forming the coating film on the coating layer in this manner, the heterocyclic group remaining in the polymeric substance (A) introduced on the surface of the base (M) may undergo the crosslinking reaction with the reactive functional group in the hydrophilic copolymer (B), so that a strong coating layer may be formed.

The thickness of the coating layer may be suitably selected depending on the object. However, in general, the thickness of the overall coating layer may preferably be from 0.001 to 100 $\mu$m.

The medical material of the present invention may be obtained by forming the coating layer, and then ring-opening the unreacted heterocyclic group remaining in the coating layer by a nucleophilic compound (N).

The nucleophilic compound (N) has no particular restriction so long as it is a compound having a functional group capable of reacting with the heterocyclic group, such as water, acidic or alkaline water, hydrogen halide, hydroxyl group-containing compound, amino group-containing compound, carboxyl group-containing compound, and mercapto group-containing compound, or a compound having two or more different these functional groups in the molecule, sodium sulfite, sodium hydrogen sulfite, and sodium thiosulfate. These compounds may be used singly, or as a mixture thereof. More preferable are sodium sulfite, sodium hydrogen sulfite, and sodium thiosulfate.

The sodium thiosulfate in the nucleophilic compound (N) is particularly preferred because of (i) low cost and high safety ($LD_{50}$ (rat, i.v.) >2.5 g/kg), (ii) high reactivity with the heterocyclic group, and (iii) the hydroxysulfonic acid group formed by adding sodium thiosulfate to the heterocyclic group is a functional group which does not adversely affect the living body.

The ring-opening of the remaining heterocyclic group with the nucleophilic compound (N) may be accomplished by a method in which a solution obtained by dissolving the nucleophilic compound (N) in a solvent is brought into contact with the coating layer. The contact may be accomplished by a method in which a base (M) on which the coating layer has been formed is immersed in the solution.

As the solvents for dissolving the nucleophilic compound (N), all the solvents may be used so long as each of them dissolves the nucleophilic compound (N) and does not modify the coating layer, and a mixed solvent is also acceptable.

The concentration of the nucleophilic compound (N) in the solution may differ depending on the characteristics of the polymeric substance (A) having the heterocyclic group in the coating layer, and the content of the heterocyclic group. However, in general, the concentration may preferably be from 0.01 to 30 wt %, and more preferably from 0.1 to 20 wt %.

Further, in the solution in which the nucleophilic compound (N) has been dissolved, a catalyst may optionally be added in order to promote the ring-opening reaction of the heterocyclic group. As the catalyst, for example, tertiary amine compounds such as triethylamine and pyridine are preferably used.

The ring-opening treatment conditions for the heterocyclic group by the nucleophilic compound (N) may suitably be selected depending on the characteristics of the formed polymeric substance (A), the content of the heterocyclic group, the type and concentration of the nucleophilic compound (N) to be used, and the presence or absence of the catalyst. The treatment temperature may preferably be from 10 to 100° C., and the treatment time may preferably be from 1 minute to 1 week.

After the aforementioned treatment, the medical material of the present invention may be obtained by sufficient washing with the solvent identical with those mentioned above, and subsequent removal of the solvent by a conventional method such as vacuum drying, forced-air drying, or heated-air drying.

The medical material of the present invention may be used for general medical instruments such as those commercially available, without limitation. For example, the present medical material may be preferably used for medical instruments to be used in direct contact with a body fluid or blood, such as blood circuit, blood bag, hemodialysis membrane, artificial vessel, artificial organ, intravascular indwelling sensor, and blood filter; medical instruments required to have both the blood compatibility and the surface lubricity, such as indwelling needle, guidewire, catheter, and applicator for an intraocular lens.

The medical material of the present invention is excellent in terms of safety because a highly toxic heterocyclic group does not remain therein. Further, there occurs no degradation of the product performance due to crosslinking between the polymeric substances caused by the residual heterocyclic group with the lapse of time. Therefore, the functions that the coating layer has are durably maintained. Further, when the polymeric substance (A) having the heterocyclic group is hydrophilic or water swellable, the polymeric substance (A) or a crosslinked product made of the polymeric substance (A) and the hydrophilic copolymer (B) chemically immobilized on the base surface forms a hydrogelated layer. Accordingly, when the layer comes in contact with a water-based medium such as a body fluid or blood, it exhibits excellent surface lubricity, as well as it also expresses high blood compatibility. Particularly, in the medical material having a coating layer formed by using both of the polymeric substance (A) and the hydrophilic copolymer (B), the reaction has been effected not only between the polymeric substances (A), but also between the two types of polymers to form a strong crosslinked structure. Therefore, even if it repeatedly receives a stress, peeling off or falling off of the polymer from the matrix surface may be inhibited, so that the performance may be durably retained.

EXAMPLES

The present invention will be described in more details by way of synthetic examples, examples, and comparative examples, but the present invention is not limited thereto.

The method for determining the contents of the epoxy group-containing monomer unit and the amino group-containing monomer unit contained in the copolymers, the method for determining each molecular weight, the measurement conditions for ESCA, the measurement conditions for ATR-IR, the lubricity evaluation method and the blood compatibility evaluation method performed in the examples are as follows:

1. Content of Epoxy Group-containing Monomer Unit 3 g of 5 wt % solution of a copolymer was added to 15 g of previously neutralized 50 vol % isopropanol aqueous solution containing 0.2 M sodium thiosulfate and phenolphthalein. The mixture was with heating and stirring on a stirrer to obtain a red-purple solution. To the obtained red-purple solution, a 0.2 N acetic acid aqueous solution was successively added for neutralization. The back titration was then performed with a 0.02 N sodium hydroxide aqueous solution, and the content of the epoxy group was calculated from the amount of an acetic acid consumed. The content (mol %) of the unit based on the amount of the epoxy group-containing monomer in the copolymer was calculated from this value.

2. Content of Amino Group-containing Monomer Unit

To 0.5 ml of 1 wt % solution of a copolymer, 2.0 ml of 0.15 M sodium borate buffer solution, 0.5 ml of 0.01M sodium sulfite aqueous solution, and 0.5 ml of 0.1 wt % trinitrobenzene sulfonic acid aqueous solution were successively added. The mixture was reacted at 37° C. for 1 hour. The absorbance of the obtained reaction solution at 420 nm was measured by an ultraviolet and visible spectrophotometer. The content of the amino group was then determined by applying the measured value to the calibration curve previously formed with allyamine hydrochloride. The content (mol %) of the unit based on the amount of the amino group-containing monomer in the copolymer was calculated from this value.

3. Molecular Weight Determination

The molecular weights in Synthesis Examples 1 and 2 were determined by the following GPC (gel permeation chromatography) conditions.

<Conditions for GPC Analysis>

A sample polymer was dissolved in a chloroform/methanol (=6/4, v/v) mixed solvent containing 0.5 wt % of lithium bromide to prepare a 0.5 wt % polymer solution. Column; PLgel 5 μm MIXED-C, two columns in series (manufactured by Polymer Laboratories Limited), eluent solvent; chloroform/methanol (=6/4, v/v) mixed solvent containing 0.5 wt % of lithium bromide, detection; differential refractometer, standard substance for determining the weight average molecular weight (Mw); PMMA (manufactured by Polymer Laboratories Limited), flow rate; 1.0 ml/minute, amount of sample solution used; 20 μl, column temperature; 40° C. A built-in molecular weight calculation program (GPC program for SC-8020) in an integrator manufactured by Tosoh Corporation was employed.

The molecular weight in Synthetic Example 7 was determined under the following GPC conditions.

<Conditions for GPC Analysis>

A sample polymer was dissolved in a phosphoric acid buffer solution (14.4 mM—$Na_2HPO_4$, 5.6 mM—$NaH_2PO_4$) to prepare a 0.5 wt % polymer solution. Column; two columns of G3000PWXL and G5000PWXL in series (manufactured by Tosoh Corporation), eluent solvent; the aforementioned phosphoric acid buffer solution, detection; differential refractometer, a standard substance for determining the weight average molecular weight (Mw); polyethylene glycol (manufactured by Polymer Laboratories Limited), flow rate; 0.5 ml/minute, amount of sample solution used; 10 µl, column temperature; 45° C. A built-in molecular weight calculation program (GPC program for SC-8020) in an integrator manufactured by Tosoh Corporation was employed.

4. Identification of Sulfur Atom by ESCA

The identification was carried out by using an X-ray photoelectron spectrometer (ESCA-3300 (manufactured by Shimadzu Co., Ltd.)) under the determination conditions in which the photoelectron emission angle was 90°.

5. Identification of Epoxy Ring by ATR-IR

The measurement was carried out by using a Fourier transform infrared spectrometer (FT/IR-7300 (manufactured by JASCO Corporation Ltd.)) and a attenuated total reflection measuring apparatus (ATR-500/M (manufactured by JASCO Corporation Ltd.)) under the determination conditions in which the angle of incidence of a prism (KRS-5) was 45°.

6. Lubricity Evaluation

<Method for Evaluating Stability of Lubricity with the Lapse of Time>

Tubes obtained in examples and comparative examples were stored at room temperature under atmosphere for 1 week or 1 month. A pair of the tubes was fixed in parallel on the bottom surface of a glass petri dish with a double-sided tape. A predetermined amount of saline was then added thereto. The friction coefficient µ was then measured by using a friction sensitivity tester (KES-SE, manufactured by KATO TECH Co., Ltd.). As a friction element, a silicon type sensor was used.

<Method for Evaluating Persistence of Lubricity>

The following durability test was carried out for evaluating the persistence of the lubricity of each of tubes obtained in Examples 5-1 to 5-3 and 6-1 to 6-3, and Comparative Examples 5 to 7, the guidewire of Comparative Example 8, and an untreated nylon tube.

A silicon plate (diameter 2.0 cm, thickness 0.5 cm) as fitted at the end of a pipe (outer diameter 2.1 cm, internal diameter 1.8 cm, height 3.5 cm) made of acrylic resin. An opening was then made in the central portion of the silicon plate with a 0.55-mm needle. The tubes or guidewires previously wetted by being immersed in a saline were inserted in the opening, and immersed in a saline and caused to slide repeatedly 100 times. The friction coefficient µ of each of the obtained samples and a silicon rubber was then determined in accordance with the foregoing method.

7. Blood Compatibility Evaluation

Tubes obtained in Examples 5-1 to 5-3 and 6-1 to 6-3, and Comparative Examples 5 to 7, the guidewire of Comparative Example 8, and an untreated nylon tube were cut to pieces having length of about 1.3 cm. Five pieces of each samples were fixed on a microcover glass (MATSUNAMI GLASS IND,. LTD, 15 mmΦ) by using a double-sided tape. These were placed in each well of a 24-well microplate, and fixed with an O-ring (internal diameter 12 mm, outer diameter 16 mm, thickness 2 to 3 mm) made of silicon rubber. 700 µl of a Hanks buffer solution was then added thereto, and the solution was equilibrated overnight. On the following day, the Hanks buffer solution was removed therefrom, and 700 µl of platelet-rich plasma (PRP) collected from a rabbit was added to each well, and allowed to stand still at room temperature for 1 hour. Then, the PRP was removed therefrom, followed by washing with 1 ml of a Hanks buffer solution 3 times. Subsequently, 1 ml of a 2.5 wt % glutaraldehyde aqueous solution was added to each well, and allowed to stand still for 2 hours to fix platelets. After a predetermined time period, the glutaraldehyde aqueous solution was removed therefrom, followed by washing with distilled water 3 times. Each of the obtained samples was freeze-dried. Gold was then sputtered thereon to observe the tube and guidewire surfaces by a scanning electron microscope. The evaluation is expressed in terms of the number of adhering platelets: VS; very small, S; small, L; large, and VL; very large.

<Synthesis of Various Copolymers>

Synthetic Example 1

37.97 g (90 mol %) of MPC and 2.03 g (10 mol %) of GMA were dissolved in 358 g of isopropanol, and the atmosphere in a reaction vessel was sufficiently replaced by a nitrogen gas. To this solution, 2.18 g of toluene solution containing 20 wt % of t-butyl peroxypivalate (the number of moles of the peroxide contained therein: 2.5 mmol) was added. The solution was then immersed in a warm bath at 60° C. for 5 hours, for heat polymerization. After cooling, the reaction solution was added dropwise in diethyl ether. The formed copolymer was recovered by filtration, followed by vacuum drying. The obtained copolymer (abbreviated hereinbelow as (P-1)) was dissolved in isopropanol to obtain a 5 wt % solution. The solution was used as the copolymer solution described in the following Examples. Further, by using this solution, the composition ratio (mol %) of MPC and GMA was determined in accordance with the method for determining the content of the epoxy group-containing monomer unit. The results are shown in Table 1. Further, the molecular weight of (P-1) was 53000.

In Table 1, (a1) denotes the hydrophilic radical polymerizable monomer (a1), (a2) denotes the monomer (a2) containing a heterocyclic group, (b1) denotes the hydrophilic radical polymerizable monomer, and (b2) denotes the radical polymerizable monomer (b2) having a functional group for ring-opening the heterocyclic group.

Synthetic Example 2

A copolymer (abbreviated hereinbelow as (P-2)) was obtained in the same manner as in Synthetic Example 1, except that the ratio of monomers MPC and GMA were changed into 33.17 g (70 mol %) and 6.83 g (30 mol %), respectively. The obtained (P-2) was dissolved in isopropanol to obtain a 5 wt % solution. The solution was used as the copolymer solution described in the following Examples. Further, by using this solution, the composition ratio (mol %) of MPC and GMA was determined in accordance with the method for determining the content of the epoxy group-containing monomer unit. The results are shown in Table 1. Further, the molecular weight of (P-2) was 64000.

Synthetic Example 3

34.93 g (90 mol %) of maleic anhydride (abbreviated hereinbelow as MA) and 5.07 g (10 mol %) of GA were dissolved in 360 g of dimethylsulfoxide, and the atmosphere in a reaction vessel was sufficiently replaced by a nitrogen gas. To this solution, 0.20 g of 2,2'-azobisisobutyronitrile was added. The solution was then immersed in a warm bath at 80° C. for 18 hours, for heat polymerization. After cooling, the solution was purified in accordance with the method of Synthetic Example 1. The obtained copolymer (abbreviated hereinbelow as (P-3)) was dissolved in tetrahydrofuran to obtain a 5 wt % solution. The solution was used as the copolymer solution described in the following Examples. Further, by using this solution, the composition ratio (mol %) of MA and GA was determined in accordance with the method for determining the content of the epoxy group-containing monomer unit. The results are shown in Table 1.

Synthetic Example 4

29.45 g (80 mol %) of N,N-dimethylacrylamide (abbreviated hereinbelow as DMAA) and 10.55 g (20 mol %) of GMA were dissolved in 360 g of dimethylsulfoxide, and the atmosphere in a reaction vessel was sufficiently replaced by a nitrogen gas. To this solution, 0.20 g of 2,2'-azobisisobutyronitrile was added. The solution was then immersed in a warm bath at 80° C. for 18 hours, for heat polymerization. After cooling, the solution was purified in accordance with the method of Synthetic Example 1. The obtained copolymer (abbreviated hereinbelow as (P-4)) was dissolved in tetrahydrofuran to obtain a 5 wt % solution. The solution was used as the copolymer solution described in the following Examples. Further, by using this solution, the composition ratio (mol %) of DMAA and GMA was determined in accordance with the method for determining the content of the epoxy group-containing monomer unit. The results are shown in Table 1.

Synthetic Example 5

31.06 g (80 mol %) of N-vinyl-2-pyrrolidone (abbreviated hereinbelow as VP) and 8.94 g (20 mol %) of GA were dissolved in 360 g of dimethylsulfoxide, and the atmosphere in a reaction vessel was sufficiently replaced by a nitrogen gas. To this solution, 0.20 g of 2,2'-azobisisobutyronitrile was added. The solution was then immersed in a warm bath at 80° C. for 18 hours, for heat polymerization. After cooling, the solution was purified in accordance with the method of Synthetic Example 1. The obtained copolymer (abbreviated hereinbelow as (P-5)) was dissolved in dichloromethane to obtain a 5 wt % solution. The solution was used as the copolymer solution described in the following Examples. Further, by using this solution, the composition ratio (mol %) of VP and GA was determined in accordance with the method for determining the content of the epoxy group-containing monomer unit. The results are shown in Table 1.

Synthetic Example 6

35.78 g (80 mol %) of ω-carboxy-dicaprolactone monoacrylate (abbreviated hereinbelow as ωCDCA) and 4.22 g (20 mol %) of GMA were dissolved in 160 g of methyl ethyl ketone, and the atmosphere in a reaction vessel was sufficiently replaced by a nitrogen gas. To this solution, 0.01 g of 2,2'-azobisisobutyronitrile was added. The solution was immersed in a warm bath at 70° C. for 10 hours, for heat polymerization. The obtained copolymer (abbreviated hereinbelow as (P-6)) was cooled, and then diluted with methyl ethyl ketone to obtain a 5 wt % solution. The solution was used as the copolymer solution described in the following Examples.

Synthetic Example 7

50.0 g (169.3 mmol, 70 mol %) of MPC and 6.79 g (72.6 mmol, 30 mol %) of allylamine hydrochloride (abbreviated hereinbelow as AAHCl) were dissolved in 370 g of distilled water, and the atmosphere in a reaction vessel was sufficiently replaced by a nitrogen gas. To this solution, 0.317 g (1.17 mmol) of 2,2'-azobis(2-amidinopropane) dihydrochloride (trade name: V-50) was added. The resulting solution was then immersed in a warm bath at 60° C. for 6 hours, for heat polymerization. After cooling, the obtained polymer solution was placed in a dialysis membrane (Spectra/Por, molecular weight cutoff=3500), and dialyzed against water for 1 week for purification, followed by freeze-drying. A part of the obtained MPC-AAHCl copolymer (abbreviated hereinbelow as (P-7)) was dissolved in distilled water to obtain a 1 wt % solution. By using this solution, the composition ratio (mol %) of MPC and AAHCl was determined in accordance with the method for determining the content of the amino group-containing monomer unit. The results are shown in Table 1. Further, the molecular weight (Mw) of (P-7) was 730000.

Synthetic Example 8

A copolymer was obtained in the same manner as in Synthetic Example 7, except that DMAA was used in place of MPC. A part of the obtained DMAA-AAHCl copolymer (abbreviated hereinbelow as (P-8)) was dissolved in distilled water to obtain a 1 wt % solution. By using this solution, the composition ratio (mol %) of DMAA and AAHCl was determined in accordance with the method for determining the content of the amino group-containing monomer unit. The results are shown in Table 1.

Synthetic Example 9

A copolymer was obtained in the same manner as in Synthetic Example 7, except that VP was used in place of MPC. A part of the obtained VP-AAHCl copolymer (abbreviated hereinbelow as (P-9)) was dissolved in distilled water to obtain a 1 wt % solution. By using this solution, the composition ratio (mol %) of VP and AAHCl was determined in accordance with the method for determining the content of the amino group-containing monomer unit. The results are shown in Table 1.

Synthetic Example 10

In accordance with the method described in Japanese National Phase PCT Laid-Open Publication No. JP-A-7-502053 (WO93/01221), MPC and 2-aminoethyl methacrylate (abbreviated hereinbelow as AEMA) were solution polymerized to obtain a copolymer. A part of the obtained MPC-AEMA copolymer (abbreviated hereinbelow as (P-10)) was dissolved in distilled water to obtain a 1 wt % solution. By using this solution, the composition ratio (mol %) of MPC and AEMA was determined in accordance with the method for determining the content of the amino group-containing monomer unit. The results are shown in Table 1.

TABLE 1

| | Synthetic Examples | | | | | | | | | |
|---|---|---|---|---|---|---|---|---|---|---|
| | 1 | 2 | 3 | 4 | 5 | 6 | 7 | 8 | 9 | 10 |
| Number of polymer | P-1 | P-2 | P-3 | P-4 | P-5 | P-6 | P-7 | P-8 | P-9 | P-10 |
| Feeding ratio | | | | | | | | | | |
| a1 | MPC | MPC | MA | DMAA | VP | ωCDCA | — | — | — | — |
| a2 | GMA | GMA | GA | GMA | GA | GMA | — | — | — | — |
| b1 | — | — | — | — | — | — | MPC | DMAA | VP | MPC |
| b2 | — | — | — | — | — | — | AAHCl | AAHCl | AAHCl | AEMA |
| a1/a2 | 90/10 | 70/30 | 90/10 | 80/20 | 80/20 | 80/20 | — | — | — | — |
| b1/b2 | — | — | — | — | — | — | 70/30 | 70/30 | 70/30 | 90/10 |
| Result | | | | | | | | | | |
| a1/a2 | 92/8 | 71/29 | 69/31 | 74/64 | 76/24 | — | — | — | — | — |
| b1/b2 | — | — | — | — | — | — | 98/2 | 99/1 | 99/1 | 91/9 | a1/a2 and b1/b2 are based on a molar ratio.

Examples 1-1 to 1-6

A tube (outer diameter 1 mm, overall length 10 cm) made of nylon was used as a base (M). This tube was immersed in a 3N sodium hydroxide aqueous solution containing 10 vol % of isopropanol at 80° C. for 30 minutes for alkaline treatment, and then sufficiently washed with water, to obtain a tube having an amino group and a carboxyl group on its surface. The tube was immersed for one minute in a 5 wt % solution of each of the copolymers (P-1) to (P-6) obtained in Synthetic Examples 1 to 6, respectively, then pulled up therefrom, and dried at room temperature for 2 hours. Subsequently, the obtained tube was subjected to a heat treatment at 90° C. for 3 to 24 hours, to manufacture a tube with each copolymer immobilized on its surface. Subsequently, the tube was immersed in a 0.2 M sodium thiosulfate aqueous solution, and allowed to stand still at room temperature for 24 hours. The tube was then taken out, and sufficiently washed with water to complete ring-opening of the residual epoxy group. The tube having the MA-GA copolymer immobilized thereon was further immersed in ethanol containing a sulfuric acid as a catalyst to ring-open the MA, and subjected to alkali cleaning by using a saline solution of sodium hydrogencarbonate to prepare a medical material.

The tube having (P-6) prepared in Synthetic Example 6 immobilized thereon was further immersed in a 10 wt % sodium hydroxide aqueous solution at room temperature for 1 minute to obtain a sample. The medical materials, i.e. the copolymer-immobilized nylon tubes thus obtained, were subjected to the surface analysis by ESCA, as Examples 1-1 to 1-6. As a result, there was observed a signal derived from the sulfur atom in sodium thiosulfate in all of the samples.

In the surface analysis by ATR-IR, the disappearance of the epoxy group peak has been confirmed in all of the samples. It has been shown from this result that the unreacted epoxy group has reacted with sodium thiosulfate and completely ring-opened.

For the obtained medical materials, the stability of lubricity with the lapse of time was evaluated in accordance with the aforementioned method. The results are shown in Table 2.

TABLE 2

| | Examples | | | | | |
|---|---|---|---|---|---|---|
| | 1-1 | 1-2 | 1-3 | 1-4 | 1-5 | 1-6 |
| Polymer used | P-1 | P-2 | P-3 | P-4 | P-5 | P-6 |
| Friction coefficient μ | | | | | | |
| Immediately after manufacturing | 0.02 | 0.02 | 0.02 | 0.03 | 0.04 | 0.02 |
| After 1 week | 0.02 | 0.02 | 0.02 | 0.03 | 0.04 | 0.02 |
| After 1 month | 0.02 | 0.02 | 0.02 | 0.03 | 0.04 | 0.02 |

Comparative Examples 1-1 to 1-6

Tubes having the various copolymers obtained in Synthetic Examples 1 to 6 immobilized thereon were manufactured in accordance with the method described in Examples 1-1 to 1-6, except that the ring opening treatment of the epoxy group by a 0.2 M sodium thiosulfate aqueous solution was not carried out. The copolymer-immobilized nylon tubes thus obtained were subjected to the surface analysis by ATR-IR, as Comparative Examples 1-1 to 1-6. As a result, there was observed a peak derived from the epoxy group in all of the samples.

For the obtained medical materials, the stability of lubricity with the lapse of time was evaluated in accordance with the aforementioned method. The results are shown in Table 3.

TABLE 3

| | Comparative Examples | | | | | |
|---|---|---|---|---|---|---|
| | 1-1 | 1-2 | 1-3 | 1-4 | 1-5 | 1-6 |
| Polymer used | P-1 | P-2 | P-3 | P-4 | P-5 | P-6 |
| Friction coefficient μ | | | | | | |
| Immediately after manufacturing | 0.02 | 0.02 | 0.02 | 0.03 | 0.04 | 0.02 |
| After 1 week | 0.03 | 0.05 | 0.03 | 0.05 | 0.05 | 0.04 |
| After 1 month | 0.06 | 0.12 | 0.05 | 0.11 | 0.12 | 0.06 |

Examples 2-1 to 2-6

A tube (outer diameter 1 mm, overall length 10 cm) made of polyurethane was immersed in a tetrahydrofuran solution containing 5 wt % of polyisocyanate (trade name: CORO- NATE L, manufactured by Nippon Polyurethane Industry Co., Ltd.) for 1 minute, then pulled up therefrom, and dried at 50° C. for 2 hours. Subsequently, the obtained tube was immersed in a 10 wt % sodium hydroxide aqueous solution, and allowed to stand still at room temperature for 30 minutes for hydrolysis of isocyanate to form an amino group on the base surface. On the tube, each of the various copolymers obtained in Synthetic Examples 1 to 6 was immobilized in accordance with the method described in Examples 1-1 to 1-6. The medical materials of the copolymer-immobilized polyurethane tubes thus obtained were subjected to the surface analysis by ESCA, as Examples 2-1 to 2-6. As a result, there was observed a signal derived from the sulfur atom in sodium thiosulfate in all of the samples. Further, in the surface analysis by ATR-IR, the disappearance of the epoxy group peak has been confirmed in all of the samples. It has been shown from this result that the unreacted epoxy group has reacted with sodium thiosulfate and completely ring-opened.

For the obtained medical materials, the stability of lubricity with the lapse of time was evaluated in accordance with the aforementioned method. The results are shown in Table 4.

TABLE 4

| | Examples | | | | | |
|---|---|---|---|---|---|---|
| | 2-1 | 2-2 | 2-3 | 2-4 | 2-5 | 2-6 |
| Polymer used | P-1 | P-2 | P-3 | P-4 | P-5 | P-6 |
| Friction coefficient $\mu$ | | | | | | |
| Immediately after manufacturing | 0.02 | 0.02 | 0.02 | 0.03 | 0.04 | 0.02 |
| After 1 week | 0.02 | 0.02 | 0.02 | 0.03 | 0.04 | 0.02 |
| After 1 month | 0.02 | 0.02 | 0.02 | 0.03 | 0.04 | 0.02 |

Comparative Examples 2-1 to 2-6

Tubes having the various copolymers obtained in Synthetic Examples 1 to 6 immobilized thereon were manufactured in accordance with the method described in Examples 2-1 to 2-6, except that the ring opening treatment of the epoxy group by a 0.2 M sodium thiosulfate aqueous solution was not carried out. The copolymer-immobilized polyurethane tubes thus obtained were subjected to the surface analysis by ATR-IR, as Comparative Examples 2-1 to 2-6. As a result, there was observed a peak derived from the epoxy group in all of the samples.

For the obtained medical materials, the stability of lubricity with the lapse of time was evaluated in accordance with the aforementioned method. The results are shown in Table 5.

TABLE 5

| | Comparative Examples | | | | | |
|---|---|---|---|---|---|---|
| | 2-1 | 2-2 | 2-3 | 2-4 | 2-5 | 2-6 |
| Polymer used | P-1 | P-2 | P-3 | P-4 | P-5 | P-6 |
| Friction coefficient $\mu$ | | | | | | |
| Immediately after manufacturing | 0.02 | 0.02 | 0.02 | 0.03 | 0.04 | 0.02 |
| After 1 week | 0.03 | 0.05 | 0.03 | 0.06 | 0.07 | 0.04 |
| After 1 month | 0.05 | 0.11 | 0.05 | 0.11 | 0.13 | 0.07 |

Examples 3-1 to 3-6

Tubes having the various copolymers obtained in Synthetic Examples 1 to 6 immobilized thereon were manufactured in accordance with the method described in Examples 2-1 to 2-6, except that a tube (outer diameter 1 mm, overall length 10 cm) made of polyvinyl chloride was used as a base (M). The medical materials, i.e. the copolymer-immobilized polyvinyl chloride tubes thus obtained, were subjected to the surface analysis by ESCA, as Examples 3-1 to 3-6. As a result, there was observed a signal derived from the sulfur atom in sodium thiosulfate in all of the samples. Further, in the surface analysis by ATR-IR, the disappearance of the epoxy group peak has been confirmed in all of the samples. It has been shown from this result that the unreacted epoxy group has reacted with sodium thiosulfate and completely ring-opened.

For the obtained medical materials, the stability of lubricity with the lapse of time was evaluated in accordance with the aforementioned method. The results are shown in Table 6.

TABLE 6

| | Examples | | | | | |
|---|---|---|---|---|---|---|
| | 3-1 | 3-2 | 3-3 | 3-4 | 3-5 | 3-6 |
| Polymer used | P-1 | P-2 | P-3 | P-4 | P-5 | P-6 |
| Friction coefficient $\mu$ | | | | | | |
| Immediately after manufacturing | 0.02 | 0.02 | 0.02 | 0.03 | 0.04 | 0.02 |
| After 1 week | 0.02 | 0.02 | 0.02 | 0.03 | 0.04 | 0.02 |
| After 1 month | 0.02 | 0.02 | 0.02 | 0.03 | 0.04 | 0.02 |

Comparative Examples 3-1 to 3-6

Tubes having the various copolymers obtained in Synthetic Examples 1 to 6 immobilized thereon were manufactured in accordance with the method described in Examples 3-1 to 3-6, except that the ring opening treatment of the epoxy group by a 0.2 M sodium thiosulfate aqueous solution was not carried out. The copolymer-immobilized polyvinyl chloride tubes thus obtained were subjected to the surface analysis by ATR-IR, as Comparative Examples 3-1 to 3-6. As a result, there was observed a peak derived from the epoxy group in all of the samples.

For the obtained medical materials, the stability of lubricity with the lapse of time was evaluated in accordance with the aforementioned method. The results are shown in Table 7.

TABLE 7

| | Comparative Examples | | | | | |
|---|---|---|---|---|---|---|
| | 3-1 | 3-2 | 3-3 | 3-4 | 3-5 | 3-6 |
| Polymer used | P-1 | P-2 | P-3 | P-4 | P-5 | P-6 |
| Friction coefficient $\mu$ | | | | | | |
| Immediately after manufacturing | 0.02 | 0.02 | 0.02 | 0.03 | 0.04 | 0.02 |
| After 1 week | 0.04 | 0.06 | 0.03 | 0.06 | 0.07 | 0.03 |
| After 1 month | 0.06 | 0.12 | 0.06 | 0.12 | 0.12 | 0.06 |

Examples 4-1 to 4-6

A tube (outer diameter 1 mm, overall length 10 cm) made of low density polyethylene was subjected to a corona treatment (irradiation energy: 1 J/cm$^2$) to form a carboxyl group on the surface of the base. On the tube, the various copolymers obtained in Synthetic Examples 1 to 6 were immobilized in accordance with the method described in Examples 1-1 to 1-6 (except that triethylamine was added to the copolymer solution as a catalyst in an amount of 0.1 wt %)) The medical materials, i.e. the copolymer-immobilized polyethylene tubes thus obtained, were subjected to the surface analysis by ESCA, as Examples 4-1 to 4-6. As a result, there was observed a signal derived from the sulfur atom in sodium thiosulfate in all of the samples. Further, in the surface analysis by ATR-IR, the disappearance of the epoxy group peak has been confirmed in all of the samples. It has been shown from this result that the unreacted epoxy group has reacted with sodium thiosulfate and completely ring-opened.

For the obtained medical materials, the stability of lubricity with the lapse of time was evaluated in accordance with the aforementioned method. The results are shown in Table 8.

TABLE 8

| | Examples | | | | | |
|---|---|---|---|---|---|---|
| | 4-1 | 4-2 | 4-3 | 4-4 | 4-5 | 4-6 |
| Polymer used | P-1 | P-2 | P-3 | P-4 | P-5 | P-6 |
| Friction coefficient $\mu$ | | | | | | |
| Immediately after manufacturing | 0.02 | 0.02 | 0.02 | 0.03 | 0.04 | 0.02 |
| After 1 week | 0.02 | 0.02 | 0.02 | 0.03 | 0.04 | 0.02 |
| After 1 month | 0.02 | 0.02 | 0.02 | 0.03 | 0.04 | 0.02 |

Comparative Examples 4-1 to 4-6

Tubes having the various copolymers obtained in Synthetic Examples 1 to 6 immobilized thereon were manufactured in accordance with the method described in Examples 4-1 to 4-6, except that the ring opening treatment of the epoxy group by a 0.2 M sodium thiosulfate aqueous solution was not carried out. The copolymer-immobilized polyethylene tubes thus obtained were subjected to the surface analysis by ATR-IR, as Comparative Examples 4-1 to 4-6. As a result, there was observed a peak derived from the epoxy group in all of the samples.

For the obtained medical materials, the stability of lubricity with the lapse of time was evaluated in accordance with the aforementioned method. The results are shown in Table 9.

TABLE 9

| | Comparative Examples | | | | | |
|---|---|---|---|---|---|---|
| | 4-1 | 4-2 | 4-3 | 4-4 | 4-5 | 4-6 |
| Polymer used | P-1 | P-2 | P-3 | P-4 | P-5 | P-6 |
| Friction coefficient $\mu$ | | | | | | |
| Immediately after manufacturing | 0.02 | 0.02 | 0.02 | 0.03 | 0.04 | 0.02 |
| After 1 week | 0.03 | 0.05 | 0.04 | 0.06 | 0.07 | 0.04 |
| After 1 month | 0.06 | 0.12 | 0.07 | 0.12 | 0.13 | 0.06 |

Examples 5-1

A tube (outer diameter 1 mm, overall length 10 cm) made of nylon subjected to an alkaline treatment in accordance with the method of Examples 1-1 to 1-6 was immersed in a isopropanol solution containing 5 wt % of (P-2) prepared in Synthetic Example 2 for 1 minute, then pulled up therefrom, and dried at room temperature for 2 hours. Subsequently, the obtained tube was subjected to a heat treatment at 90° C. for 3 to 24 hours, to manufacture a tube with (P-2) immobilized thereon. Subsequently, the tube was immersed in a ethanol solution containing 2 wt % of (P-7) prepared in Synthetic Example 7 for 1 minute, then pulled up therefrom, and dried at room temperature for 2 hours. The tube was further subjected to a heat treatment at 90° C. for 3 to 24 hours. The obtained tube having both (P-2) and (P-7) immobilized thereon was immersed in a 0.2 M sodium thiosulfate aqueous solution, and allowed to stand still at room temperature for 24 hours. The tube was then taken out, and sufficiently washed with water, for completing ring-opening of the residual epoxy group. The crosslinking immobilized film formed on the base surface by the foregoing operation is referred to as MPC-AAHCl/MPC-GMA-SO$_3$Na.

The manufactured MPC-AAHCl/MPC-GMA-SO$_3$Na-immobilized nylon tube was subjected to a surface analysis by ESCA. As a result, there was observed a signal derived from the sulfur atom in sodium thiosulfate. Further, in the surface analysis by ATR-IR, the disappearance of the epoxy group peak has been confirmed. It has been shown from this result that the unreacted epoxy group has reacted with sodium thiosulfate and completely ring-opened.

For the obtained medical material, evaluations were carried out in accordance with the aforementioned method for evaluating the stability of lubricity with the lapse of time, method for evaluating the persistence of lubricity and blood compatibility evaluation. The results are shown in Table 10.

Example 5-2

A DMAA-AAHCl/MPC-GMA-SO$_3$Na-immobilized nylon tube was manufactured in accordance with the method described in Example 5-1, except that the tetrahydrofuran solution containing 2 wt % of (P-8) prepared in Synthetic Example 8 was employed in place of the ethanol solution containing 2 wt % of (P-7). The tube was subjected to the surface analysis by ESCA. As a result, there was observed a signal derived from the sulfur atom in sodium thiosulfate. Further, in the surface analysis by ATR-IR, the disappearance of the epoxy group peak has been confirmed. It has been shown from this result that the unreacted epoxy group has reacted with sodium thiosulfate and completely ring-opened.

For the obtained medical material, evaluations were carried out in accordance with the aforementioned method for evaluating the stability of lubricity with the lapse of time, method for evaluating the persistence of lubricity and blood compatibility evaluation. The results are shown in Table 10.

Example 5-3

A VP-AAHCl/MPC-GMA-SO$_3$Na-immobilized nylon tube was manufactured in accordance with the method described in Example 5-1, except that the dichloromethane solution containing 2 wt % of (P-9) prepared in Synthetic Example 9 was employed in place of the ethanol solution containing 2 wt % of (P-7). The tube was subjected to the surface analysis by ESCA. As a result, there was observed a signal derived from the sulfur atom in sodium thiosulfate. Further, in the surface analysis by ATR-IR, the disappearance of the epoxy group peak has been confirmed. It has been shown from this result that the unreacted epoxy group has reacted with sodium thiosulfate and completely ring-opened.

For the obtained medical material, evaluations were carried out in accordance with the aforementioned method for evaluating the stability of lubricity with the lapse of time, method for evaluating the persistence of lubricity and blood compatibility evaluation. The results are shown in Table 10.

Example 6-1

An isopropanol solution containing 5 wt % of (P-2) prepared in Synthetic Example 2 and an ethanol solution containing 2 wt % of (P-7) prepared in Synthetic Example 7 were mixed in a ratio by weight of 1:1. Into the obtained mixed polymer solution, a tube (outer diameter 1 mm, overall length 10 cm) made of nylon subjected to an alkaline treatment in accordance with the method of Examples 1-1 to 1-6 was immersed for 1 minute, then pulled up therefrom, and dried at room temperature for 2 hours. Subsequently, the obtained tube was subjected to a heat treatment at 90° C. for 3 to 24 hours. The obtained tube having both (P-2) and (P-7) immobilized thereon was immersed in a 0.2 M sodium thiosulfate aqueous solution, and allowed to stand still at room temperature for 24 hours. Then, the tube was taken out, and sufficiently washed with water, for completing ring-opening of the residual epoxy group. The crosslinking immobilized film formed on the base surface by the foregoing operation is referred to as MPC-AAHCl+MPC-GMA-$SO_3Na$.

The manufactured MPC-AAHCl+MPC-GMA-$SO_3Na$-immobilized nylon tube was then subjected to a surface analysis by ESCA. As a result, there was observed a signal derived from the sulfur atom in sodium thiosulfate. Further, in the surface analysis by ATR-IR, the disappearance of the epoxy group peak has been confirmed. It has been shown from this result that the unreacted epoxy group has reacted with sodium thiosulfate and completely ring-opened.

For the obtained medical material, evaluations were carried out in accordance with the aforementioned method for evaluating the stability of lubricity with the lapse of time, method for evaluating the persistence of lubricity and blood compatibility evaluation. The results are shown in Table 10.

Example 6-2

A DMAA-AAHCl+MPC-GMA-$SO_3Na$-immobilized nylon tube was manufactured in accordance with the method described in Example 6-1, except that the tetrahydrofuran solution containing 2 wt % of (P-8) prepared in Synthetic Example 8 was employed in place of the ethanol solution containing 2 wt % of (P-7). The tube was subjected to the surface analysis by ESCA. As a result, there was observed a signal derived from the sulfur atom in sodium thiosulfate. Further, in the surface analysis by ATR-IR, the disappearance of the epoxy group peak has been confirmed. It has been shown from this result that the unreacted epoxy group has reacted with sodium thiosulfate and completely ring-opened.

For the obtained medical material, evaluations were carried out in accordance with the aforementioned method for evaluating the stability of lubricity with the lapse of time, method for evaluating the persistence of lubricity and blood compatibility evaluation. The results are shown in Table 10.

Example 6-3

A VP-AAHCl+MPC-GMA-$SO_3Na$-immobilized nylon tube was manufactured in accordance with the method described in Example 6-1, except that the dichloromethane solution containing 2 wt % of (P-9) prepared in Synthetic Example 9 was employed in place of the ethanol solution containing 2 wt % of (P-7). The tube was subjected to the surface analysis by ESCA. As a result, there was observed a signal derived from the sulfur atom in sodium thiosulfate. Further, in the surface analysis by ATR-IR, the disappearance of the epoxy group peak has been confirmed. It has been shown from this result that the unreacted epoxy group has reacted with sodium thiosulfate and completely ring-opened.

For the obtained medical material, evaluations were carried out in accordance with the aforementioned method for evaluating the stability of lubricity with the lapse of time, method for evaluating the persistence of lubricity and blood compatibility evaluation. The results are shown in Table 10.

Comparative Example 5

A tube (outer diameter 1 mm, overall length 10 cm) made of nylon subjected to an alkaline treatment in accordance with the method of Examples 1-1 to 1-6 was immersed in the ethanol solution containing 2 wt % of (P-7) prepared in Synthetic Example 7 for 1 minute, then pulled up therefrom, and dried at room temperature for 2 hours. Subsequently, the obtained tube was subjected to a heat treatment at 90° C. for 3 to 24 hours, to manufacture a nylon tube coated with the copolymer.

For the obtained medical material, evaluations were carried out in accordance with the aforementioned method for evaluating the persistence of lubricity and blood compatibility evaluation. The results are shown in Table 10.

Comparative Example 6

A tube (outer diameter 1 mm, overall length 10 cm) made of polyurethane was immersed in a tetrahydrofuran solution containing 5 wt % of polyisocyanate (trade name: CORONATE L, manufactured by Nippon Polyurethane Industry Co., Ltd.) for 1 minute, then pulled up therefrom, and dried at 50° C. for 2 hours. Subsequently, the obtained tube was immersed in a chloroform solution containing 4 wt % of polyvinyl pyrrolidone for 1 minute, then pulled up, and dried at room temperature for 2 hours. Subsequently, the tube was subjected to a heat treatment at 80° C. for 5 hours, to manufacture a polyurethane tube having polyvinyl pyrrolidone bonded thereto.

For the obtained medical material, evaluations were carried out in accordance with the aforementioned method for evaluating the persistence of lubricity and blood compatibility evaluation. The results are shown in Table 10.

Comparative Example 7

A polyimide tube having an acrylic acid graft polymerized thereon was allowed to react with (P-10) prepared in Synthetic Example 10 by using 1-ethyl-3-(3-dimethylaminopropyl)carbodiimide as a condensation agent. Consequently, a polyimide tube having the MPC-AEMA copolymer described in Japanese National Phase PCT Laid-Open Publication No. JP-A7-502053 (WO93/01221) immobilized thereon was manufactured.

For the obtained medical material, evaluations were carried out in accordance with the aforementioned method for evaluating the persistence of lubricity and blood compatibility evaluation. The results are shown in Table 10.

Comparative Example 8

A hydrophilic guidewire (outer diameter 0.89 mm, manufactured by Terumo Corp.) was obtained. The guidewire was prepared by coating a core wire of nickel-titanium alloy with polyurethane, and further coating the wire with a maleic anhydride polymeric substance.

For the guidewire, evaluations were carried out in accordance with the aforementioned method for evaluating the persistence of lubricity and blood compatibility evaluation. The results are shown in Table 10.

smaller than with the untreated sample, the adhesion of platelets was observed even before the durability test. The platelets adhered thereto were deformed by activation, and extended their pseudopodia.

TABLE 10

|  | Examples | | | | | | Comparative Examples | | | | Untreated |
|---|---|---|---|---|---|---|---|---|---|---|---|
|  | 5-1 | 5-2 | 5-3 | 6-1 | 6-2 | 6-3 | 5 | 6 | 7 | 8 | nylon |
| Friction coefficient μ | | | | | | | | | | | |
| Immediately after manufacturing | 0.02 | 0.03 | 0.04 | 0.02 | 0.03 | 0.03 | — | — | — | — | — |
| After 1 week | 0.02 | 0.03 | 0.04 | 0.02 | 0.03 | 0.03 | — | — | — | — | — |
| After 1 month | 0.02 | 0.03 | 0.04 | 0.02 | 0.03 | 0.03 | — | — | — | — | — |
| Friction coefficient μ | | | | | | | | | | | |
| Before durability test | 0.02 | 0.03 | 0.04 | 0.02 | 0.03 | 0.03 | 0.02 | 0.04 | 0.03 | 0.02 | 0.49 |
| After durability test | 0.02 | 0.03 | 0.04 | 0.02 | 0.03 | 0.03 | 0.47 | 0.45 | 0.40 | 0.03 | 0.50 |
| Number of platelets adhered | | | | | | | | | | | |
| Before durability test | VS | S or VS | S or VS | VS | S or VS | S or VS | VS | S | VS | L | VL |
| After durability test | VS | S or VS | S or VS | VS | S or VS | S or VS | VL | VL or L | VL or L | L | VL |

As seen from the results of Tables 2, 4, 6, 8 and 10, the copolymer-immobilized tubes of the present invention, which have been subjected to the ring-opening treatment of the residual epoxy group by sodium thiosulfate, exhibited no change of the friction coefficient μ with the lapse of time, i.e., exhibited excellent stability with the lapse of time. On the other hand, the tubes obtained in Comparative Examples 1-1 to 1-6, Comparative Examples 2-1 to 2-6, Comparative Examples 3-1 to 3-6, and Comparative Examples 4-1 to 4-6, which have not been subjected to the ring-opening treatment of the residual epoxy group by sodium thiosulfate, resulted in increase of the friction coefficient μ with the lapse of time and loss of the initial lubricity.

Further, as seen from the results of Table 10, the tubes of the present invention exhibited good surface lubricity, which was held even after the durability test. Among them, the MPC-AAHCl/MPC-GMA-SO$_3$Na-immobilized nylon tube obtained in Example 5-1 and the MPC-AAHCl+MPC-GMA-SO$_3$Na-immobilized nylon tube obtained in Example 6-1 exhibited particularly excellent lubricity. Although the nylon tubes prepared in Comparative Examples 5 to 7, and the guidewire of Comparative Example 8 exhibited small frictional resistance value before the durability test, they exhibited increased amount of the frictional resistance value after the durability test.

It has been shown from the foregoing that the medical material of the present invention exhibits an excellent surface lubricity, as well as the persistence thereof.

Further, with any of the tubes of the examples of the present invention, the number of adhering platelets is smaller as compared with the untreated samples. Further, the tendency thereof was held even after the durability test. Among them, the MPC-AAHCl/MPC-GMA-SO$_3$Na-immobilized nylon tube obtained in Example 5-1 and the MPC-AAHCl+MPC-GMA-SO$_3$Na-immobilized nylon tube obtained in Example 6-1 exhibited no adhesion with platelets, and exhibited an excellent blood compatibility. Although the tubes of Comparative Examples 5 to 7 exhibited almost no adhesion of platelets prior to the durability test, they exhibited adhesion of a large number of platelets after the durability test. As to the guidewire of Comparative Example 8, although the number of adhering platelets was As seen from the foregoing, the medical material of the present invention has excellent blood compatibility and maintains the functions thereof stably even after the durability test.

What is claimed is:

1. A medical material obtained by forming a coating layer with a coating material containing a polymeric substance (A) having a heterocyclic group represented by the formula (1) on at least a part of a surface of a medical material base, and ring-opening the heterocyclic group remaining in the coating layer by a nucleophilic compound (N):

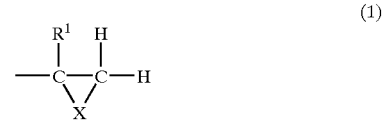

(1)

wherein X denotes O, NH, or S, and R$^1$ denotes H or CH$_3$,
wherein the polymeric substance (A) is a copolymer obtained by polymerizing a mixture of polymerizable monomers containing a hydrophilic radical polymerizable monomer (a1) and a monomer (a2) having a heterocyclic group represented by the formula (1).

2. The medical material according to claim 1, wherein the hydrophilic radical polymerizable monomer (a1) has a group represented by the formula (2):

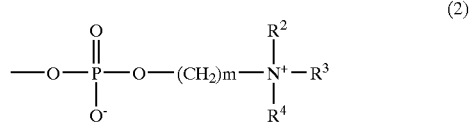

(2)

wherein R$^2$, R$^3$, and R$^4$ are the same or different groups, and denote a hydrogen atom or a monovalent hydrocarbon group having 1 to 4 carbon atoms; and m is an integer of 2 to 4.

3. The medical material according to claim 1, wherein the hydrophilic radical polymerizable monomer (a1) comprises 2-(methacryloyloxy)ethyl-2-(trimethylammonio)ethyl phosphate.

4. A medical material obtained by forming a coating layer with a coating material containing a polymeric substance (A) having a heterocyclic group represented by the formula (1) on at least a part of a surface of a medical material base, and ring-opening the heterocyclic group remaining in the coating layer by a nucleophilic compound (N):

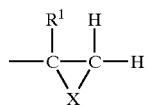
(1)

wherein X denotes O, NH, or S, and $R^1$ denotes H or $CH_3$,
wherein the coating material contains a hydrophilic copolymer (B) having a reactive functional group capable of reacting with the heterocyclic group, wherein the hydrophilic copolymer (B) has a group represented by the formula (2) as a side chain:

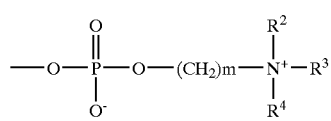
(2)

wherein $R^2$, $R^3$, $R^4$ are the same or different groups, and denote a hydrogen atom or a monovalent group having 1 and 4 carbon atoms; and m is an integer of 2 to 4.

5. The medical material according to claim 4, wherein the hydrophilic copolymer (B) is a copolymer containing a structural unit obtained by reacting 2-(methacryloyloxy)ethyl-2'-trimethylammonio)ethyl phosphate.

6. A medical material obtained by forming a coating layer with a coating material containing a polymeric substance (A) having a heterocyclic group represented by the formula (1) on at least a part of a surface of a medical material base, and ring-opening the heterocyclic group remaining in the coating layer by a nucleophilic compound (N):

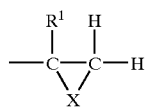
(1)

wherein X denotes O, NH, or S, and $R^1$ denotes H or $CH_3$, wherein the nucleophilic compound (N) is selected from the group consisting of sodium thiosulfate, sodium sulfate, sodium hydrogen sulfate, and mixtures thereof.

7. A method for producing the medical material obtained by forming a coating layer with a coating material containing a polymeric substance (A) having a heterocyclic group represented by the formula (1) on at least a part of a surface of a medical material base, providing on the coating layer a coating film configured with a hydrophilic copolymer (B) having a reactive functional group capable of reacting with the heterocyclic group, and ring-opening the heterocyclic group remaining in the coating layer by a nucleophilic compound (N):

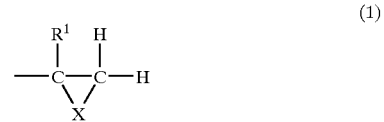
(1)

wherein X denotes O, NH, or S, and $R^1$ denotes H or $CH_3$, said method comprising
(a) applying a coating material containing a polymeric substance (A) having a heterocyclic group represented by the formula (1) on at least a part of a surface of a medical material base, followed by
(b) heating to form a coating layer,
(c) applying on the coating layer a solution of a hydrophilic copolymer (B) having a reactive functional group capable of reacting with the heterocyclic group, followed by
(d) heating to provide a coating film configured with the hydrophilic copolymer (B), and
(e) bringing the coating layer into contact with a solution containing a nucleophilic compound (N) to ring-open the heterocyclic group remaining in the coating layer.

8. A medical material obtained by forming a coating layer with a coating material containing a polymeric substance (A) having a heterocyclic group represented by the formula (1) on at least a part of a surface of a medical material base, providing on the coating layer a coating film configured with a hydrophilic copolymer (B) having a reactive functional group capable of reacting with the heterocyclic group, and ring-opening the heterocyclic group remaining in the coating layer by a nucleophilic compound (N):

(1)

wherein X denotes O, NH, or S, and $R^1$ denotes H or $CH_3$, wherein the polymeric substance (A) is a copolymer obtained by polymerizing a mixture of polymerizable monomers containing a hydrophilic radical polymerizable monomer (a1) and a monomer (a2) having a heterocyclic group represented by the formula (1).

9. A medical material obtained by forming a coating layer with a coating material containing a polymeric substance (A) having a heterocyclic group represented by the formula (1) on at least a part of a surface of a medical material base, providing on the coating layer a coating film configured with a hydrophilic copolymer (B) having a reactive functional group capable of reacting with the heterocyclic group, and ring-opening the heterocyclic group remaining in the coating layer by a nucleophilic compound (N):

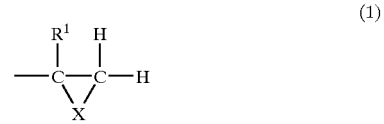
(1)

wherein X denotes O, NH, or S, and $R^1$ denotes H or $CH_3$, wherein the hydrophilic copolymer (B) has a group represented by the formula (2) as a side chain:

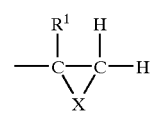
(2)

wherein $R^2$, $R^3$, and $R^4$ are the same or different groups, and denote a hydrogen atom or a monovalent hydrocarbon group having 1 and 4 carbon atoms; and m is an integer of 2 to 4.

10. The medical material according to claim 9 wherein the hydrophilic copolymer (B) is a copolymer containing a structural unit obtained by reacting 2-(methacryloyloxy) ethyl-2'-(trimethylammonio)ethyl phosphate.

11. A medical material obtained by forming a coating layer with a coating material containing a polymeric substance (A) having a heterocyclic group represented by the formula (1) on at least a part of surface of a medical material base, providing on the coating layer a coating film configured with a hydrophilic copolymer (B) having a reactive functional group capable of reacting with the heterocyclic group, and ring-opening the heterocyclic group remaining in the coating layer by a nucleophilic compound (N):

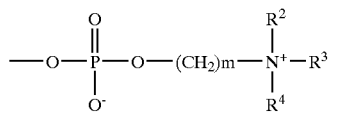
(1)

wherein X denotes O, NH, or S, and $R^1$ denotes H or $CH_3$, wherein the nucleophilic compound (N) is selected from the group consisting of sodium thiosulfate, sodium sulfite, sodium hydrogen sulfite, and mixtures thereof.

* * * * *

UNITED STATES PATENT AND TRADEMARK OFFICE
CERTIFICATE OF CORRECTION

PATENT NO.     : 6,828,028 B1
DATED          : December 7, 2004
INVENTOR(S)    : Hiroki Fukui et al.

It is certified that error appears in the above-identified patent and that said Letters Patent is hereby corrected as shown below:

Title page,
Item [75], Inventors, please delete "Hiroki Fukui, Tsukuba (JP)" and substitute
-- Hiroki Fukui, Ibaraki, (JP) --; "Ken Suzuki, Tsukuba (JP)" and substitute
-- Ken Suzuki, Ibaraki, (JP) --; "Kenshiro Shuto, Tsukuba (JP) and substitute
-- Kenshiro Shuto, Ibaraki (JP) --; "Nobuyuki Yamamoto, Tsukuba (JP)"
and substitute -- Nobuyuki Yamamoto, Ibaraki, (JP) --; "Nobuo Nakabayashi,
Matsudo (JP)" and substitute -- Nobuo Nakabayashi, Chiba, (JP) --; "**Kazuhiko
Ishihara, Kodaira (JP)" and substitute -- Kazuhiko Ishihara**, Tokyo, (JP) --;
Item [30], Foreign Application Priority Data, please add the following:
-- July 28, 1999 (JP) ……………….. 11-214191 --

Signed and Sealed this

Twenty-ninth Day of March, 2005

JON W. DUDAS
*Director of the United States Patent and Trademark Office*